(12) United States Patent
Yamamoto et al.

(10) Patent No.: US 6,776,888 B2
(45) Date of Patent: Aug. 17, 2004

(54) BIOSENSOR

(75) Inventors: Tomohiro Yamamoto, Hirakata (JP); Miwa Hasegawa, Nara (JP); Motokazu Watanabe, Katano (JP); Shin Ikeda, Katano (JP); Shiro Nankai, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 240 days.

(21) Appl. No.: 10/089,289

(22) PCT Filed: Jul. 26, 2001

(86) PCT No.: PCT/JP01/06472

§ 371 (c)(1),
(2), (4) Date: Mar. 26, 2002

(87) PCT Pub. No.: WO02/010735

PCT Pub. Date: Jul. 2, 2002

(65) Prior Publication Data

US 2002/0148726 A1 Oct. 17, 2002

(30) Foreign Application Priority Data

Jul. 31, 2000 (JP) ........................................ 2000-232385

(51) Int. Cl.[7] ............................................. G01N 27/327
(52) U.S. Cl. ............................... 204/403.09; 204/403.06
(58) Field of Search ....................... 204/403.01, 403.05, 204/403.06, 403.09, 403.1, 403.14

(56) References Cited

U.S. PATENT DOCUMENTS

| 3,607,092 A | | 9/1971 | Neff et al. |
| 4,477,575 A | | 10/1984 | Vogel et al. |
| 5,522,977 A | * | 6/1996 | Shieh .................... 204/403.06 |
| 5,609,749 A | | 3/1997 | Yamauchi et al. |
| 5,658,444 A | | 8/1997 | Black et al. |
| 5,779,867 A | * | 7/1998 | Shieh .................... 204/403.12 |

FOREIGN PATENT DOCUMENTS

| EP | 0 856 586 A1 | 8/1998 |
| EP | 1 118 675 A2 | 7/2001 |
| EP | 1 182 456 A2 | 2/2002 |
| EP | 1 235 068 A1 | 8/2002 |
| JP | 63-058149 | 3/1988 |
| JP | 01-134246 | 5/1989 |
| JP | 02-062952 | 3/1990 |
| JP | 09-318588 | 12/1997 |
| JP | 11-508693 A | 7/1999 |
| WO | WO 97/38126 A1 | 10/1997 |

\* cited by examiner

*Primary Examiner*—Alex Noguerola
(74) *Attorney, Agent, or Firm*—Akin Gump Strauss Hauer & Feld, L.L.P.

(57) ABSTRACT

The present invention provides a biosensor that enables highly-accurate measurement of a sample solution including a solid component like hemocytes and has a little variation in response. The biosensor includes: an insulating base plate, an electrode system having at least a working electrode and a counter electrode provided on the base plate, a cover member that is combined with the base plate to define a sample solution supply pathway for leading a sample solution from a sample supply unit to the electrode system, a reaction reagent system including at least an oxidation-reduction enzyme and an electron mediator, and a filter disposed between the electrode system and the sample supply unit in the sample solution supply pathway. The biosensor has a space that encircles surface of the filter in an area from one end of the filter close to the sample supply unit to the other end of the filter close to the electrode system. This arrangement effectively prevents the solid component like hemocytes from flowing into the electrode system without being filtered out by the filter.

17 Claims, 9 Drawing Sheets

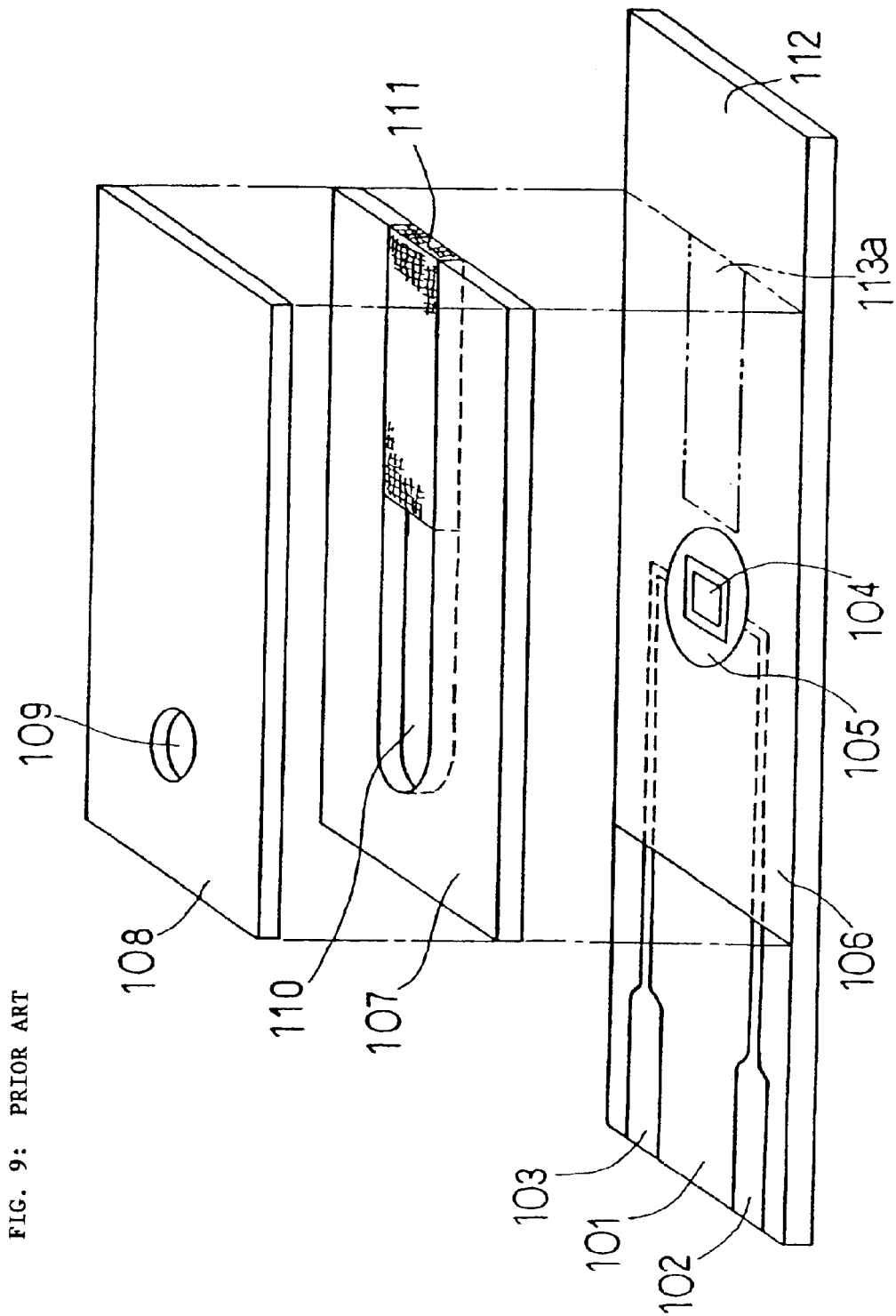
FIG. 9: PRIOR ART

BIOSENSOR

TECHNICAL FIELD

The present invention relates to a biosensor that carries out high-speed, highly-accurate, simple determination of a target object in a sample.

BACKGROUND ART

A biosensor has been proposed to determine a specific component in a sample by a simple procedure without any dilution or stirring the sample solution (Japanese Laid-Open Patent Publication No. 2-062952).

In this biosensor, an electrode system including a measurement electrode or a working electrode, a counter electrode, and a reference electrode is formed on an insulating base plate, for example, by screen printing. An enzyme reaction layer including a hydrophilic polymer, an oxidation-reduction enzyme, and an electron mediator is then formed on the electrode system. A buffer may be added to this enzyme reaction layer according to the requirements.

When a sample solution containing a substrate is added dropwise onto the enzyme reaction layer in the biosensor thus constructed, the enzyme reaction layer is dissolved to cause a reaction of the enzyme with the substrate, which results in reduction of the electron mediator. After completion of the enzyme reaction, the reduced electron mediator is oxidized electrochemically, and the concentration of the substrate included in the sample solution is calculated from the observed value of oxidation current.

In principle, the biosensor is applicable to measurement of diverse substances by selecting an appropriate enzyme that reacts with a target substance of measurement as the substrate. For example, when glucose oxidase is used as the oxidation-reduction enzyme, the biosensor is constructed to measure the concentration of glucose in blood. This is widely used as a glucose sensor. Application of cholesterol oxidase gives a biosensor that measures cholesterol in serum.

The value of serum cholesterol generally used for the index of diagnosis is the sum of the concentrations of cholesterol and cholesterol ester. The cholesterol ester is, however, not the substrate of the oxidation reaction with cholesterol oxidase. In order to measure the value of serum cholesterol as the index of diagnosis, an additional process is thus required to change the cholesterol ester to cholesterol. Cholesterol esterase is used as the enzyme that catalyzes this process.

The biosensor including cholesterol esterase and cholesterol oxidase in its enzyme reaction layer is used to measure the total concentration of cholesterol in serum.

The measurement of cholesterol is affected by cholesterol that is present in the cell membrane. The coexistence of a surface active agent with cholesterol esterase in the reaction reagent layer is preferable to enhance the reactivity. The surface active agent destroys the cell membrane in many cases, and there is a possibility that the substances inside the cell directly or indirectly affect the enzyme reaction or the electrode reaction. From this point of view, it is preferable that the enzyme reaction and the subsequent electrode reaction proceed in plasma or serum in the cholesterol sensor. In biosensors other than the cholesterol sensor, the presence of hemocytes in blood may also affect the response. It is accordingly ideal that the enzyme reaction and the electrode reaction proceed in a solution free of hemocytes.

Centrifugation is a known method to separate plasma or serum from whole blood. The centrifugation method, however, takes a rather long time and requires complicated operations.

U.S. Pat. No. 3,607,092 discloses a membrane used for testing blood. This membrane has a thin film layer that has permeability to liquids but impermeability to solids like hemocytes and giant molecules like protein. Namely this thin film functions to filter out the hemocytes. However, since the solid component is accumulated on the thin film with the passage of blood, a large area of the thin film layer is required to obtain filtrate of a certain amount sufficient for the reaction of the biosensor. The above-mentioned thin film is thus not sufficient.

U.S. Pat. No. 4,477,575 discloses an apparatus for and a method of separating serum from whole blood passing through a glass fiber filter. The method of separating serum from whole blood with a fiber or porous filter is applicable to the biosensor. This method, however, does not make the hemocytes kept in the filter but simply slows down the flow of hemocytes for separation of plasma. In the case of application of this method to the biosensor, a certain quantity of filtered plasma or serum sufficient for the reaction in the biosensor should be obtained, before the hemocytes are flown out of the filter. For this purpose, a specific setting that satisfies this condition should be applied for the length of the filter in the direction of blood flow.

The filter satisfying this condition is disposed between one portion of the biosensor with the electrode system and the reaction reagent system and another portion of the biosensor for supplying blood as a sample to construct the biosensor having the ability of filtering the hemocytes. FIG. 9 shows a biosensor of such construction. FIG. 9 is a decomposed perspective view of the biosensor without the reaction reagent layer.

In the example of FIG. 9, silver paste is printed on an insulating base plate 101 composed of polyethylene terephthalate by screen printing to form leads 102 and 103 and the base of an electrode system. Conductive carbon paste including a resin binder is printed on the base plate 101 to form the electrode system including a working electrode 104 and a counter electrode 105, while insulting paste is printed to form an insulating layer 106. The working electrode 104 is connected to the lead 102, and the counter electrode 105 to the lead 103. The insulating layer 106 makes the exposed area of the working electrode 104 and the counter electrode 105 constant, and partly covers the leads.

The process arranges the insulating base plate 101 with the electrode system, a cover 108 with an air vent 109, a spacer 107, and a filter 111 having the ability of filtering hemocytes at the positional relationship shown by the one-dot chain line and joins together to assemble a biosensor. The filter 111 is cut to fit a sample solution supply pathway, which is defined by a slit 110 of the spacer 107 between the cover 108 and the insulating base plate 101. Numeral 113a represents a portion at which the filter 111 is in contact with the insulating base plate. The filter 111 is disposed between the electrode system and a sample supply unit 112 on the base plate without covering over the electrode system including the working electrode 104 and the counter electrode 105 in the sample solution supply pathway.

In the biosensor having the above construction, blood added dropwise onto the sample supply unit 112 soaks into an end of the filter 111 close to the sample supply unit. In the filter, the permeation rate of hemocytes is less than the permeation rate of plasma as the liquid component, and the plasma accordingly soaks out of the end of the filter close to the electrode system. The soak-out plasma dissolves reaction reagents, which include enzymes and are carried at a specific position covering over the electrode system or on the rear face of the cover immediately above the specific position, and fills the whole sample solution supply pathway from the vicinity of the electrode system to the air vent 109. When the whole sample solution supply pathway is filled with the liquid, the flow of the liquid in the filter 111 stops, so that the hemocytes do not reach the end of the filter close to the electrode system but are retained at the current position.

Through the filtration of hemocytes, the reaction reagent layer dissolved in plasma chemically reacts with a target component included in the plasma, cholesterol in the case of the cholesterol sensor. After elapse of a preset time, the value of electric current is measured by means of the electrode reaction. This determines the component in the plasma.

In this prior art biosensor, part of the blood added dropwise to the sample supply unit 112 is not absorbed through the end of the filter 111 close to the sample supply unit. But the blood including hemocytes is transferred through the gap between the sample solution supply pathway and the filter 111 to reach the reaction reagent layer. This causes the hemocytes or some component in the hemocytes to react with the reaction reagent and give a significant error to the measurement.

Bonding the filter 111 to the sample solution supply pathway via an adhesive may prevent the transfer of blood through the gap between the filter 111 and the sample solution supply pathway.

The adhesive may, however, affect the blood components. This method also requires application of the adhesive on either the surface of the filter 111 or the sample solution supply pathway, which results in the complicated manufacturing process.

The object of the present invention is thus to solve the drawbacks discussed above by improving a biosensor with a filter that is capable of filtering a solid component like hemocytes.

More specifically the object of the present invention is to provide a biosensor that has stable response by allowing a sample added to the sensor to soak into a filter and making only a sample solution transmitted through the filter reach a reaction reagent layer and an electrode system.

DISCLOSURE OF INVENTION

A biosensor in accordance with the present invention includes: an insulating base plate, an electrode system that is provided on the base plate and has at least a working electrode and a counter electrode, a cover member that is combined with the base plate to define a sample solution supply pathway for leading a sample solution from a sample supply unit to the electrode system, a reaction reagent system including at least an oxidation-reduction enzyme and an electron mediator, and a filter disposed between the electrode system and the sample supply unit in the sample solution supply pathway, the biosensor having a space that encircles surface of the filter in an area from one end of the filter close to the sample supply unit to the other end of the filter close to the electrode system.

In one preferred mode of the present invention, the sample supply unit is provided on the base plate, and the sample solution supply pathway is formed along the base plate and the cover member.

In this mode, it is desirable that the space surrounding the surface of the filter has a width of not less than 0.5 mm. The width of the space less than 0.5 mm may cause blood transmitted through a gap between the base plate and/or the cover member forming the sample solution supply pathway and the filter to reach the area of the space by means of capillarity. The preferable width of the space ranges from 0.5 mm to 5.0 mm. The width over 5.0 mm may undesirably lead to deformation of the filter under vibrations applied to the sensor. More specifically, the preferable width is 1.0 mm to 3.0 mm.

In another preferred mode of the present invention, the sample supply unit is provided on the cover member, and the sample solution supply pathway is disposed in a direction of gravity from the sample supply unit. In this mode, it is preferable that the width of the space surrounding the surface of the filter is not less than 100 $\mu$m and is smaller than the thickness of the filter.

The filter used here is a porous body having spaces connecting with one another in a three-dimensional manner, and the porous body moves blood from the sample supply unit toward the sample solution supply pathway by capillarity while functions to filter hemocytes based on a difference between flow resistances of plasma and the hemocytes. A non-woven fabric preferably composed of a hydrophilic fiber, such as fiber glass, cellulose, or pulp, filter paper, or another porous body may be applied for the filter.

The arrangement of the present invention is preferably applied for a cholesterol sensor in which the oxidation-reduction enzyme is cholesterol oxidase.

In the cholesterol sensor, it is preferable that the reaction reagent system includes an enzyme having an ability of hydrolyzing cholesterol ester. It is also preferable that the enzyme having the ability of hydrolyzing cholesterol ester is cholesterol esterase and that the reaction reagent system includes a surface active agent.

It is desirable that part or all of the cover member and the insulating base plate are transparent.

BRIEF DESCRIPTION OF THE DRAWINGS

FIG. 9 is a decomposed perspective view illustrating a prior art biosensor without a reaction reagent layer.

BEST MODES FOR CARRYING OUT THE INVENTION

Figure 1:
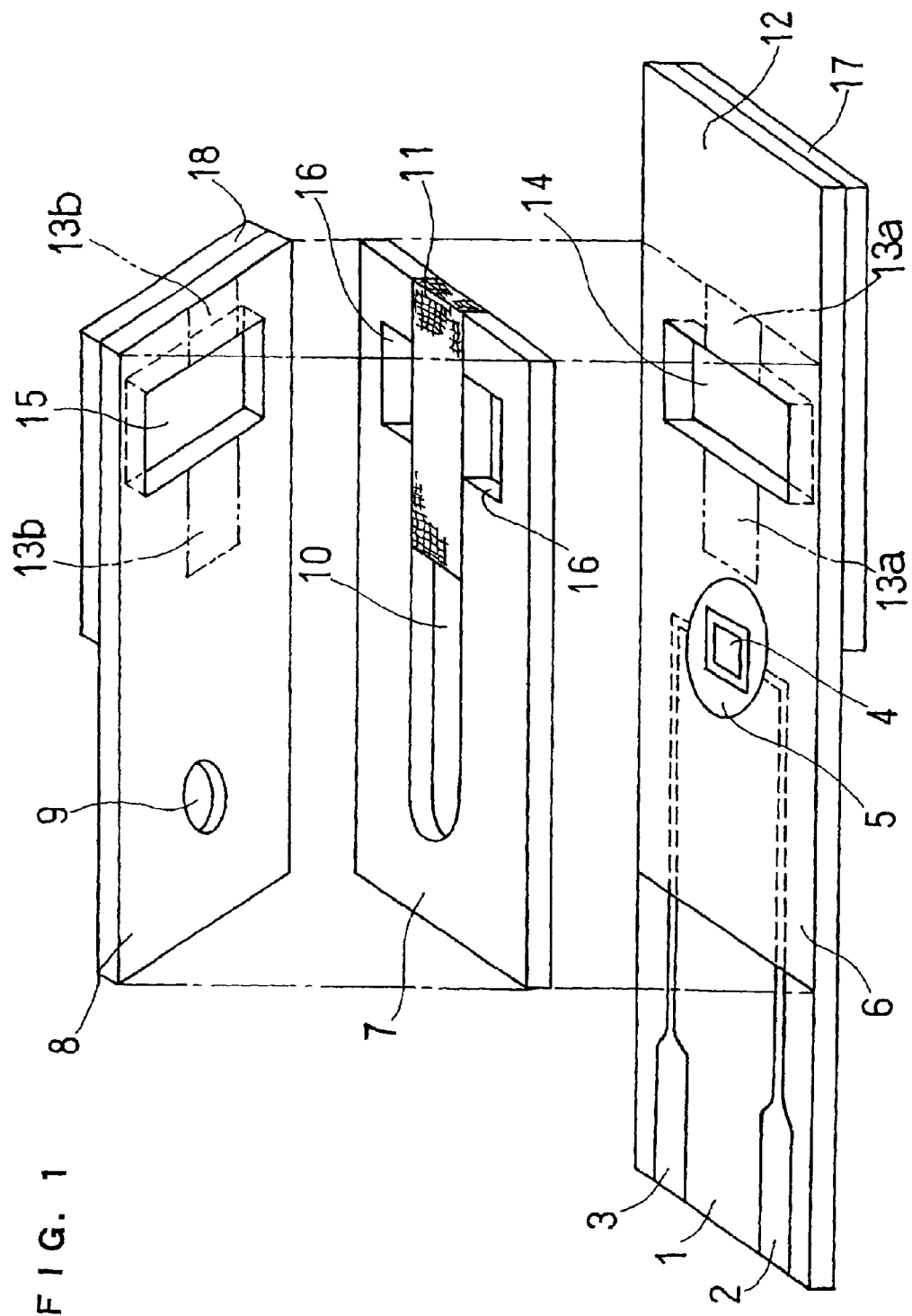
FIG. 1 is a decomposed perspective view illustrating a biosensor without a reaction reagent layer in one embodiment of the present invention.

As discussed above, a biosensor of the present invention has a sample solution supply pathway that is defined by a combination of a base plate and a cover member, and a filter that is disposed in the sample solution supply pathway between a sample supply unit provided on either the base plate or the cover member and an electrode system on the base plate, the biosensor having a space surrounding the surface of the filter in an area from one end of the filter close to the sample supply unit to the other end of the filter close to the electrode system. Namely there is a specific area, in which the whole circumference of the surface of the filter is not in contact with either of the base plate and the cover member that form the sample solution supply pathway.

One aspect of the present invention is a biosensor, which includes: an insulating base plate, an electrode system that is provided on the base plate and has at least a working electrode and a counter electrode, a cover member that is combined with the base plate to define a sample solution supply pathway for leading a sample solution from a sample supply unit on the base plate to the electrode system on the base plate, a reaction reagent system that includes at least an oxidation-reduction enzyme and an electron mediator and is provided on or in the vicinity of the electrode system, and a filter disposed between the electrode system and the sample supply unit in the sample solution supply pathway, the biosensor having a space that encircles surface of the filter in an area from one end of the filter close to the sample supply unit to the other end of the filter close to the electrode system.

Another aspect of the present invention is a biosensor, which includes: an insulating base plate, an electrode system that is provided on the base plate and has at least a working electrode and a counter electrode, a cover member that is combined with the base plate, a sample solution supply pathway that is formed between the cover member and the base plate for leading a sample solution from a sample supply unit on the cover member to the electrode system on the base plate, a reaction reagent system that includes at least an oxidation-reduction enzyme and an electron mediator and is provided on or in the vicinity of the electrode system, and a filter disposed between the electrode system and the sample supply unit in the sample solution supply pathway, the biosensor having a space that encircles surface of the filter in an area from one end of the filter close to the sample supply unit to the other end of the filter close to the electrode system.

In the above construction, the sample solution like blood added dropwise to the sample supply unit is absorbed by the filter and flows through the sample solution supply pathway toward the electrode system and the reaction reagent layer, while the solid substance like the hemocytes is filtered out by the filter. Only the sample solution from which the solid component like the hemocytes is filtered out accordingly reaches the electrode system. In the sample solution supply pathway close to the sample supply unit, however, part of the sample solution may not be absorbed by the filter but may directly flow from a little gap in the contact area of the filter with the sample solution supply pathway into the sample solution supply pathway. Even in such cases, the gap encircling the surface of the filter effectively prevents the sample solution from further flowing toward the electrode system. Therefore, the sample solution including the solid substance like hemocytes is prevented from flowing through the space toward the electrode system. It is preferable that the reaction reagent system is provided on or in the vicinity of the electrode system in the sample solution supply pathway.

A diversity of enzymes may be used for the oxidation-reduction enzyme included in the reaction reagent system. Such examples include glucose oxidase, lactate oxidase, and cholesterol oxidase.

In the case of measurement of serum cholesterol, cholesterol oxidase and an enzyme having an ability of hydrolyzing cholesterol ester are used. Cholesterol esterase and lipoprotein lipase are examples of the enzyme having the ability of hydrolyzing cholesterol ester. Especially cholesterol esterase is preferable since it quickly changes cholesterol ester to cholesterol in the presence of an appropriate surface active agent.

When the reaction reagent system includes the enzyme having the ability of hydrolyzing cholesterol ester, it is preferable that the reaction reagent system further includes a surface active agent for enhancing the ability of the enzyme. This desirably shortens the time required for the enzyme reaction.

Any of n-octyl-$\beta$-D-thioglucoside, polyethylene glycol monododecyl ether, sodium cholate, dodecyl-$\beta$-maltoside, sucrose monolaurate, sodium deoxycholate, sodium taurodeoxycholate, N,N-bis(3-D-gluconamide propyl) cholamide, N,N-bis(3-D-gluconamide propyl) deoxycholamide, polyoxyethylene-p-t-octylphehyl ether (TritonX-100) may be used for the surface active agent for enhancing the activity of cholesterol esterase.

When an electrochemically stable metal like platinum is applied for the electrode system of the biosensor, the observed value of oxidation current does not include an error. Such metals are, however, expensive. In disposal-type sensors, the electrode system includes a silver electrode composed of, for example, silver paste, and a carbon electrode obtained by covering the silver electrode with carbon paste. When the sample solution includes a surface active agent, the sample solution soaks into carbon particles by the function of the surface active agent. This may lower the activity of the carbon electrode. This also causes the sample solution to be in contact with the silver electrode. When a voltage is applied to the working electrode under such conditions, an oxidation reaction may occur on the silver electrode to generate electric current and give a positive error to the observed value of electric current.

One proposed method to suppress such phenomena covers the surface of the electrode system with a hydrophilic polymer. The hydrophilic polymer makes the introduced sample solution a viscous layer, which prevents the sample solution from coming into contact with the electrodes.

Examples of the hydrophilic polymer include carboxymethyl cellulose, polyvinyl pyrrolidone, polyvinyl alcohol, ethyl cellulose, hydroxypropyl cellulose, gelatin, polyacrylic acid and its salts, starch and its derivatives, polymers of maleic anhydride or its salts, polyacrylamide, methacrylate resin, and poly-2-hydroxyethyl methacrylate.

Other than the method using the hydrophilic polymer, the following method may be applied to suppress the effects of the surface active agent discussed above. A specific part of the electrode system that comes into contact with the sample solution is made of only carbon paste. Silver paste for ensuring the electric conductivity is used only for the part covered with an insulating layer. The hydrophilic polymer layer is not required in such printed electrodes. The hydrophilic polymer, however, also functions to prevent protein in the sample solution or the mixture of the sample solution and the reaction reagent from being adsorbed on the surface of the electrode and lowering the activity of the electrode reaction. It is accordingly preferable to use the hydrophilic polymer even in such printed electrodes.

When silver and carbon are used for the electrode system of the biosensor, an electron mediator should be added to the reaction reagent layer.

Any water-soluble compound that mediates transfer of electrons between the enzyme and the electrode, for example, potassium ferricyanide, p-benzoquinone, phenazine methosulfate, and ferrocene derivatives (oxidation type) may be applied for the electron mediator.

A two electrode system using only the working electrode and the counter electrode and a three electrode system using the reference electrode in addition to the two electrodes is applicable to measure the oxidation current. The three electrode system is preferable to ensure the higher accuracy of measurement.

The present invention is described in detail by referring to some embodiments. The drawings are only illustrative and the relative dimensions of the respective elements do not reflect the accurate sizes.

Figure 2:
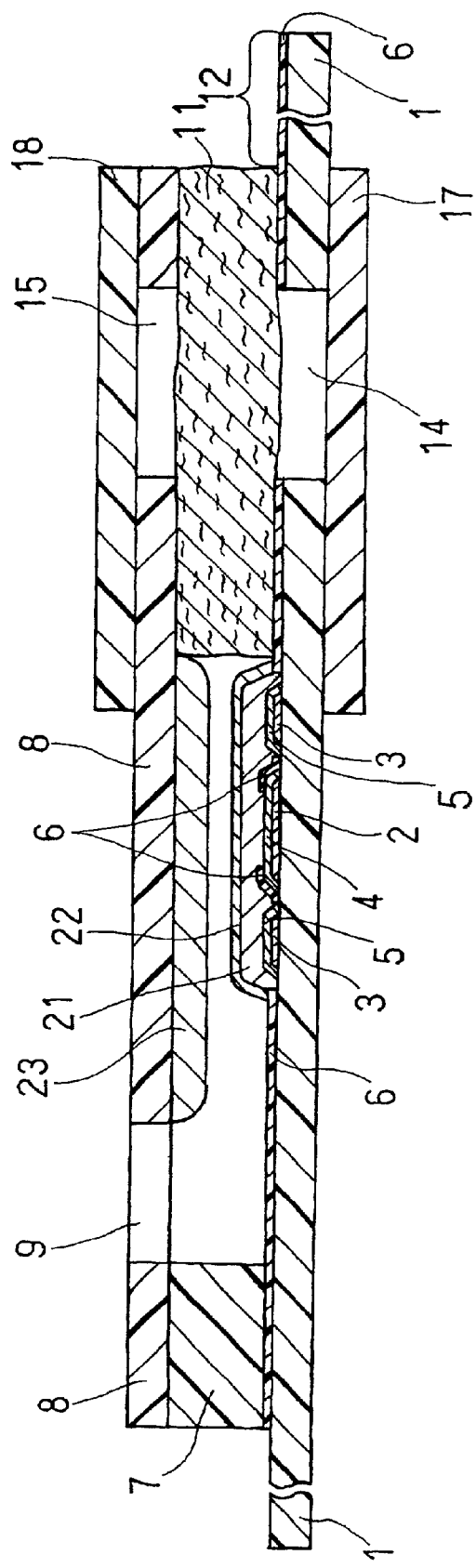
FIG. 2 is a vertical sectional view illustrating the biosensor of FIG. 1.

FIG. 1 is a decomposed perspective view illustrating a biosensor in one embodiment of the present invention, and FIG. 2 is a vertical sectional view of the biosensor.

Silver paste is printed on an insulating base plate 1 of polyethylene terephthalate by screen printing to form leads 2 and 3 and the base of an electrode system. Electrically conductive carbon paste containing a resin binder is further printed on the base plate 1 to form an electrode system including a working electrode 4 and a counter electrode 5, while insulating paste is printed to form an insulating layer 6. The working electrode 4 is connected to the lead 2, and the counter electrode 5 to the lead 3. The insulating layer 6 makes the exposed areas of the working electrode 4 and the counter electrode 5 constant, and partly covers the leads.

The insulating base plate 1 with the electrode system, a cover 8 with an air vent 9, s spacer 7, and a filter 11 having the ability of filtering hemocytes are bonded according to the positional relationship shown by the one-dot chain line, thereby to prepare a biosensor. A sample solution supply pathway running along the base plate 1 and the cover 8 is defined by a slit 10 of the spacer 7 between the base plate 1 and the cover 8. The filter 11 is cut into the size fitting the sample solution supply pathway and is disposed between the electrode system and a sample supply unit not to cover the electrode system. Numerals 13a and 13b represent parts at which the filter 11 is in contact with the insulating base plate 1 and the cover 8, respectively.

There is a specific area from one end of the filter 11 close to the sample supply unit 12 to the other end close to the electrode system, in which the surface of the filter 11 is not in contact with any of the base plate 1, the spacer 7, and the cover 8 that define the sample solution supply pathway. In order to make this area, the base plate 1 and the spacer 7 respectively have through holes 14 and 15 at corresponding positions, and the cover 8 has two notches 16 connecting with the slit 10. Lids 17 and 18 are attached to the outer faces of the base plate 1 and the cover 8 to respectively cover the through holes 14 and 15 formed in the base plate 1 and the cover 8. The through holes 14 and 15 and the notches 16,16 form the space encircling the surface of the filter 11.

The through holes 14 and 15 can exert their functions even in the open condition, although they are closed with the lids 17 and 18 in this embodiment. The filter 11 is exposed to outside in the open condition. There is accordingly some possibility that evaporation of the sample solution through the exposed part causes the liquid passing through the filter and reaching the electrode system to flow back. The lids 17 and 18 are accordingly provided to cover the through holes of the base plate and the cover. In the case where both the base plate and the cover are sufficiently thick, recesses that do not require the lids 17 and 18 may be formed instead of the through holes.

When the sample solution is added dropwise onto the sample supply unit 12 on the base plate to come into contact with an end of the filter 11 close to the sample supply unit, the sample solution soaks into the filter 11. The filter 11 removes the solid component like hemocytes, and the plasma flows through the sample solution supply pathway and is led into the sensor. The plasma fills up the whole sample solution supply pathway from the vicinity of the electrode system to the portion of the air vent 9, while dissolving therein the reaction reagents carried at a specific position covering over the electrode system or on the rear face of the cover immediately above the specific position. When the whole sample solution supply pathway is filled with the liquid, the flow of the liquid in the filter 11 stops. At this moment, the hemocytes do not reach the end of the filter 11 close to the electrode system but are retained at the current position. Thus the filter 11 is designed to produce such a difference in flow resistance between plasma and hemocytes that the hemocytes have not yet reached the end of the filter when the plasma has passed through the filter and filled up the whole sample solution supply pathway.

In this embodiment, the length between one end of the sample solution supply pathway defined by the slit 10 on the sample supply unit to the outer circumference of the air vent 9 is 12.5 mm. The slit 10 has the width of 2.0 mm and the depth of 0.1 mm.

The dimensions of the through holes 14 and 15 expressed as (dimension in the direction perpendicular to the longitudinal direction of the base plate)×(dimension in the longitudinal direction of the base plate) are 4.0×3.0 mm, and the dimensions of the notches 16 are also 4.0×3.0 mm. Both the base plate and the cover have the thickness of 0.35 mm, and the thickness of the spacer is 0.1 mm. Accordingly, the filter 11 is surrounded by space having a thickness of 0.35 mm above and below the filter 11 and a thickness of 2.0 mm on both right and left sides of the filter 11, and a width of 3.0 mm in the flowing direction of the sample solution (hereinafter referred to as the width of the space). The space is located at a position 1 mm apart from the end of the sample supply unit and 3.0 mm apart from the end of the electrode system. The above dimensions show just an example of the preferred embodiment, and are not restrictive in any sense.

FIG. 2 is a vertical sectional view illustrating the assembled biosensor. A hydrophilic polymer layer 21 and an electron mediator layer 22 covering over the hydrophilic polymer layer 21 are formed on the electrode system on the base plate 1. The filter 11 is disposed in the sample solution supply pathway defined by the slit 10 of the spacer 7. The end of the filter 11 may be or may not be in contact with the electrode system, but must not be in contact with and be apart from the working electrode 4 in the electrode system. In the sample solution supply pathway, a layer 23 including enzymes and a surface active agent is formed in a specific area interposed between an end of the filter 11 close to the electrode system and the air vent 9 on the rear face of the cover 8. The contact of this layer 23 with the end of the filter 11 facilitates the flow of the sample solution into the layer 23, although the contact is not essential.

Figure 3:
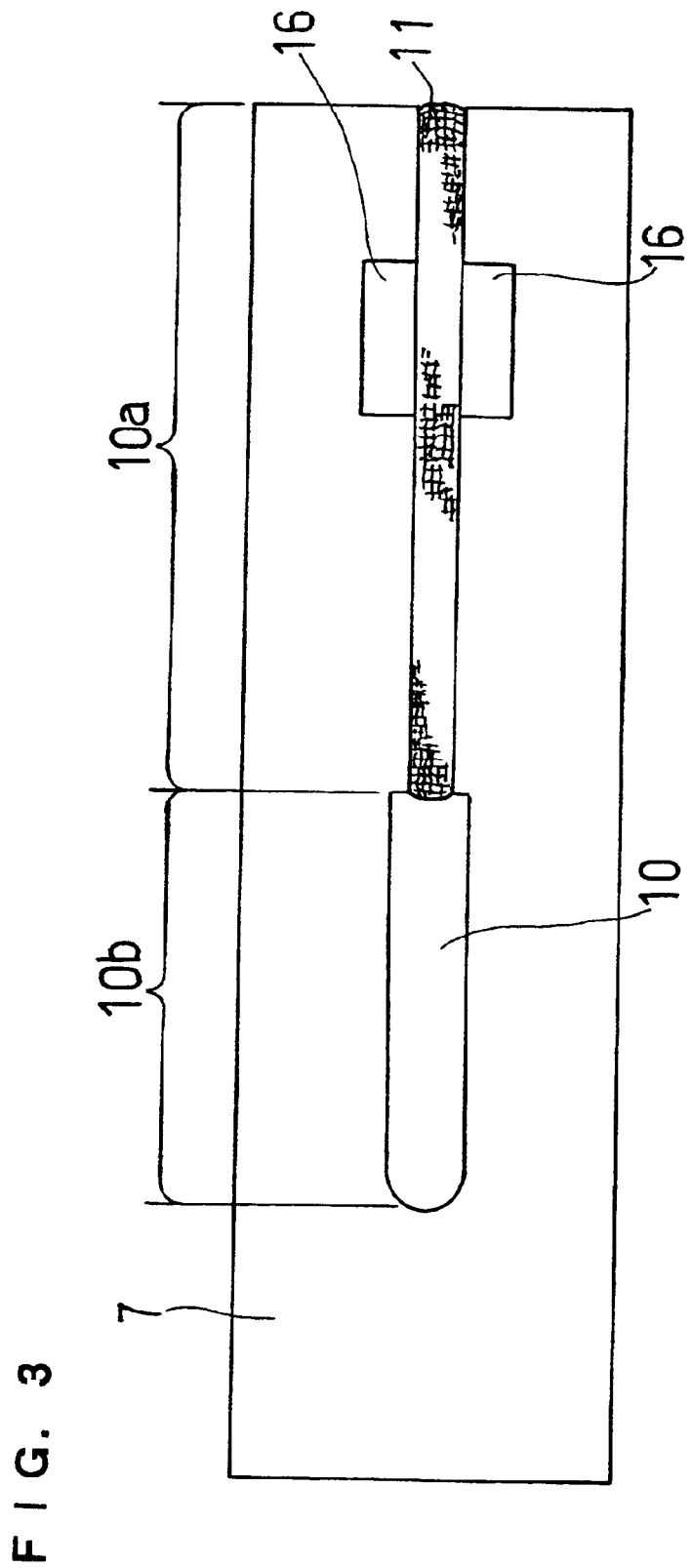
FIG. 3 is a plan view illustrating a main part of a biosensor in another embodiment of the present invention.

FIG. 3 is a plan view illustrating the positional relationship between the spacer and the filter in a biosensor in another embodiment of the present invention. The slit 10 for defining the sample solution supply pathway has a portion 10a in which the filter is fitted, and a portion 10b that has the electrode system and receives a flow-in sample passing through the filter. The width of the portion 10a is different from the width of the portion 10b. More specifically, in the embodiment of FIG. 3, the width of the portion 10a with the filter fitted therein is narrower than the width of the portion 10b with the electrode system.

Figure 4:
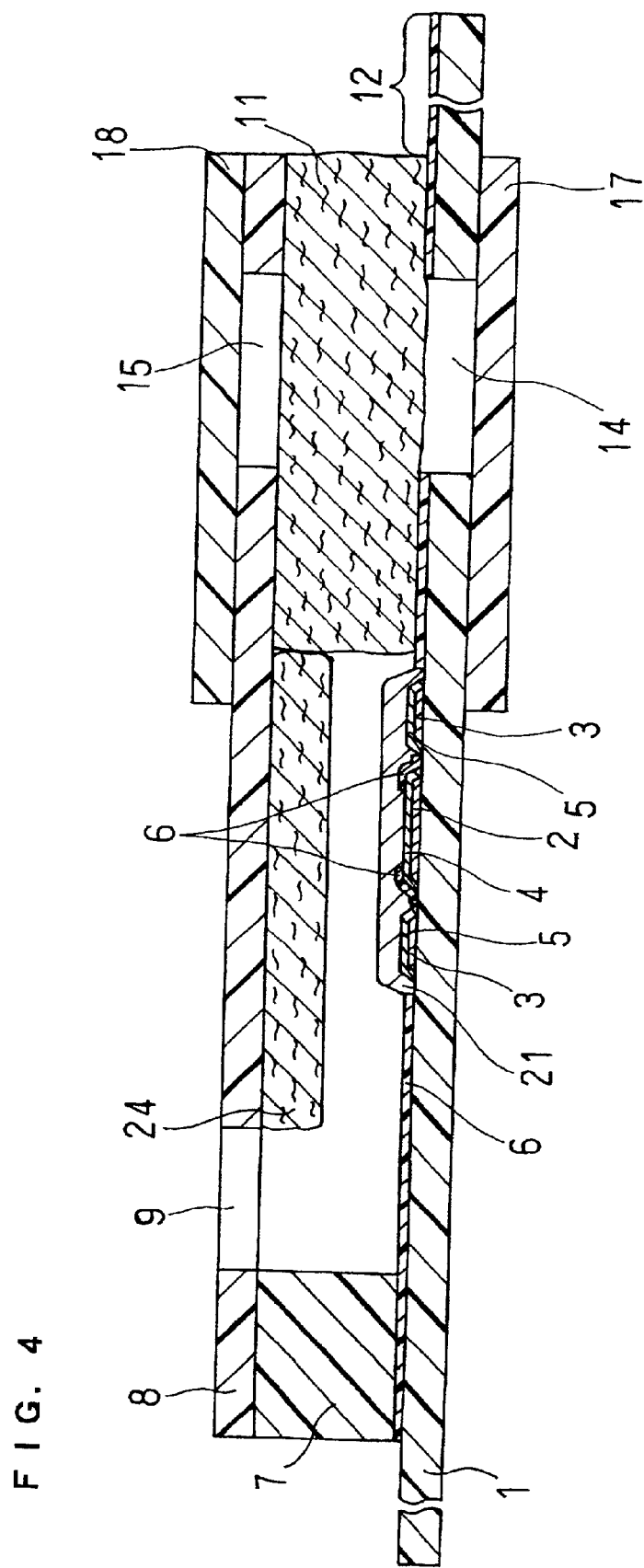
FIG. 4 is a vertical sectional view illustrating a biosensor in still another embodiment of the present invention.

FIG. 4 is a vertical sectional view illustrating a biosensor in still another embodiment of the present invention. This biosensor has a similar structure to that of FIG. 2 with a different arrangement of the reaction reagent layer. In the structure of this embodiment, only the hydrophilic polymer layer 21 is formed on the electrode system. A porous carrier 24 impregnated with enzymes, a surface active agent, and an electron mediator is provided on the cover 8 to be in contact with an end of the filter 11.

Figure 5:
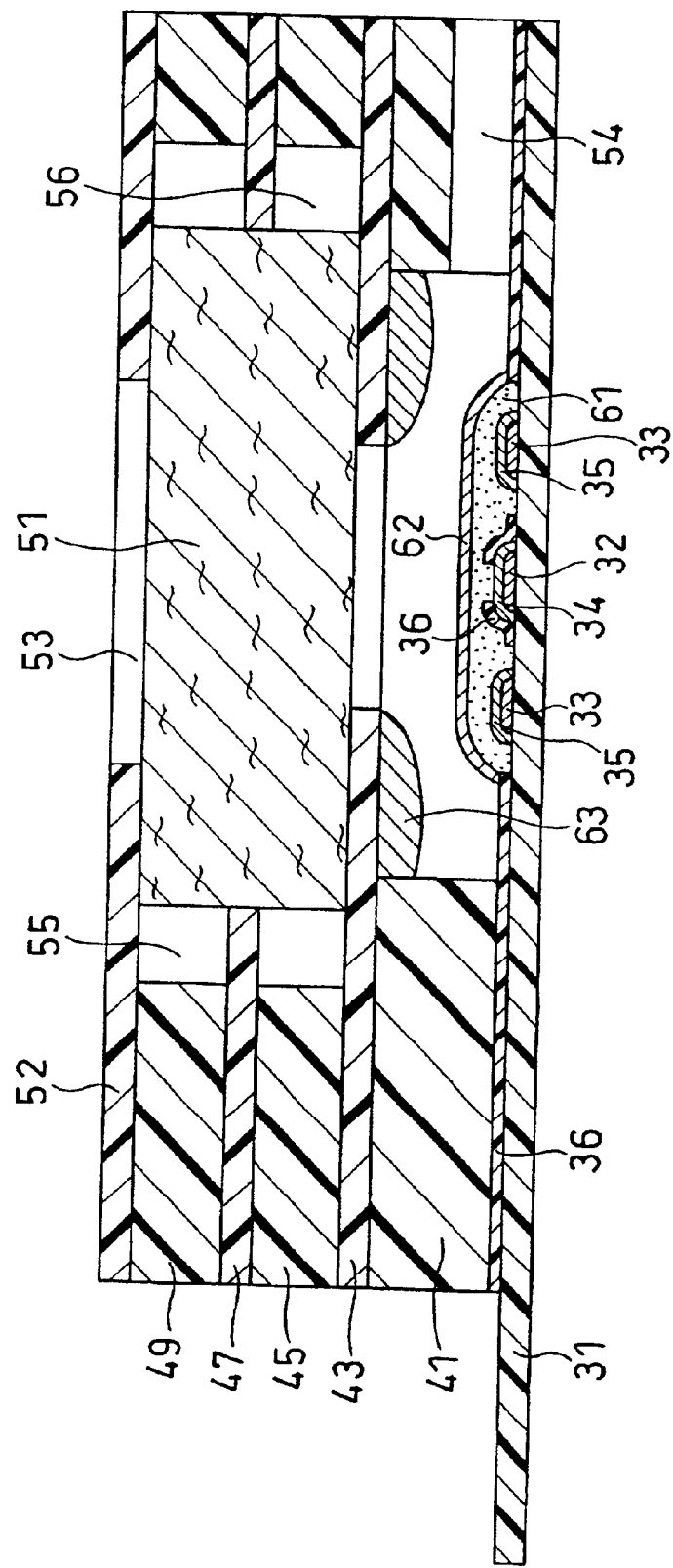
FIG. 5 is a vertical sectional view illustrating a biosensor in another embodiment of the present invention.
Figure 6:
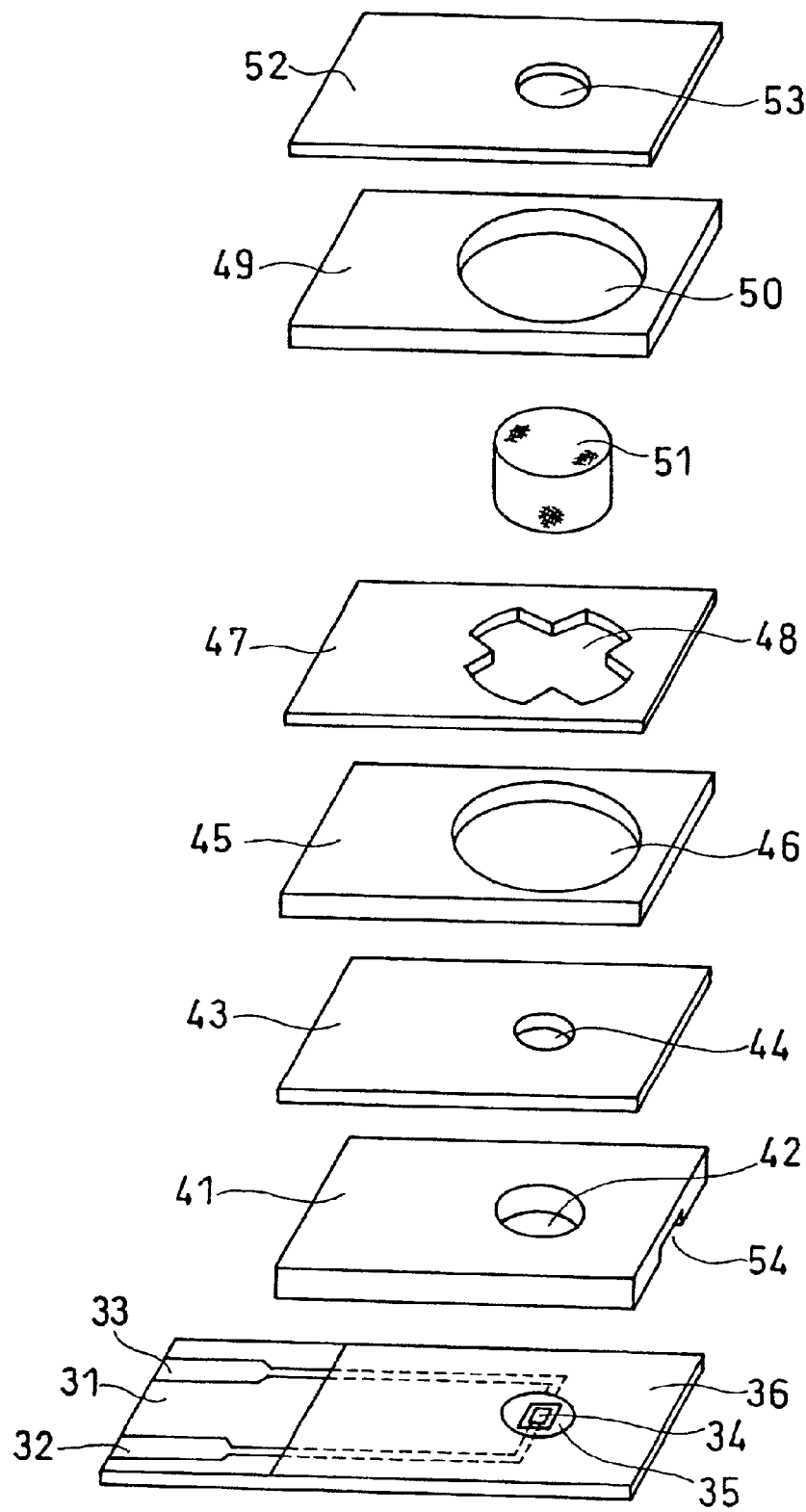
FIG. 6 is a decomposed perspective view illustrating the biosensor of FIG. 5.

FIG. 5 is a vertical sectional view illustrating a biosensor in another embodiment of the present invention, and FIG. 6 is a decomposed perspective view of the biosensor without its reaction reagent layer.

As in the structure of FIG. 1, leads 32 and 33, a working electrode 34 and a counter electrode 35 connecting with the respective leads, and an insulating layer 36 are formed on an insulating base plate 31. A combination of multiple spacers 41, 43, 45, 47, and 49 with a cover 52 is provided on the base plate 31. A filter 51 is interposed between the spacer 43 and the cover 52. A through hole 53 in the cover 52 forms a sample supply unit. Through holes 42, 44, 46, 48, and 50 formed in the spacers 41, 43, 45, 57, and 49 define a sample solution supply pathway running in the direction of gravity. Since the through holes 46 and 50 in the spacers 45 and 49 have diameters greater than the diameter of the filter 51, spaces surrounding the filter 51 are formed around the filter 51, as shown by numerals 55 and 56. The spacer 47 is partly in contact with the outer circumference of the filter 51 to locate the filter 51. The spacer 41 has an air vent 54 that connects the end of the sample solution supply pathway to the air. The sample solution is introduced in the direction of gravity by means of capillarity into the sample solution supply pathway, which connects the through hole 53 disposed above the electrode system to function as the sample supply unit to the electrode system. The movement of the sample solution stops when the plasma passing through the filter 51 reaches the electrode system.

The thickness of the spacers 49 and 45 that specify the height of the spaces 55 and 56 surrounding the filter 51 is preferably not less than 100 μm. The reaction of the sample solution with the reagents proceeds in the through hole 42 formed in the spacer 41. The preferable thickness of the spacer 41 ranges 100 to 200 μm. The orientation of the sample solution supply pathway in the direction of gravity enables the sample to pass through the filter by means of the gravity and quickly reach the reaction reagent layer.

In this embodiment, a CMC layer 61 and an electron mediator layer 62 are formed on the electrode system. A layer 63 including enzymes and a surface active agent is formed on the rear face of the spacer 43.

Figure 7:
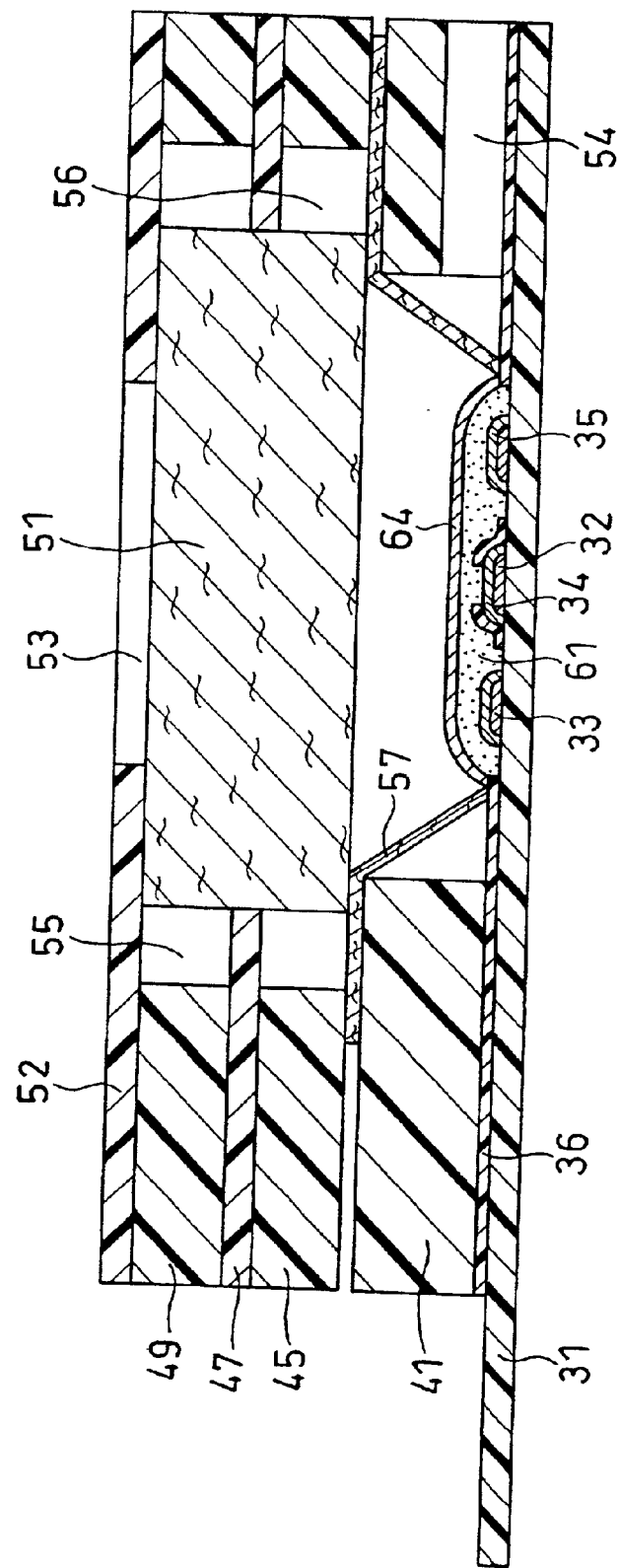
FIG. 7 is a vertical sectional view illustrating a biosensor in still another embodiment of the present invention.
Figure 8:
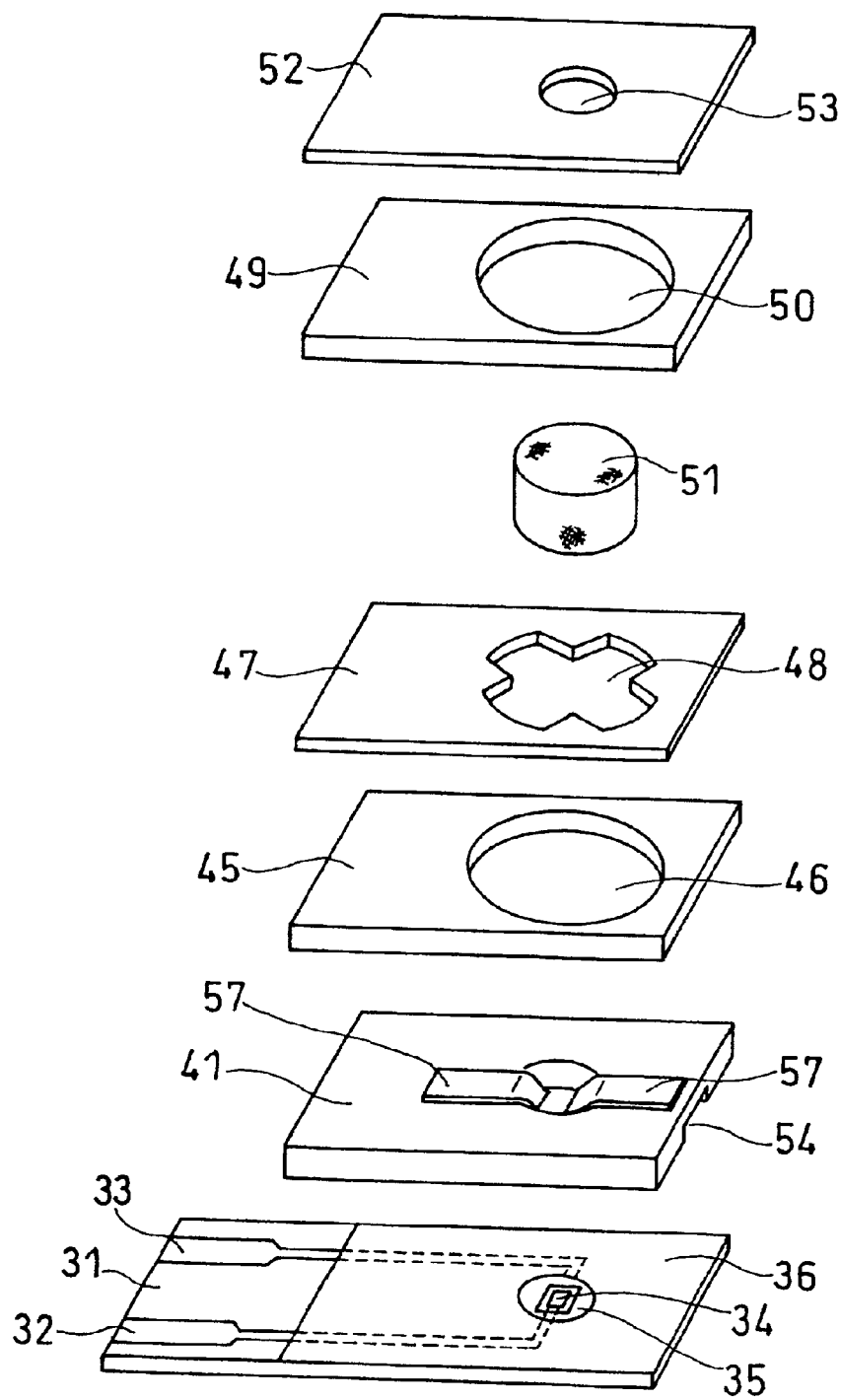
FIG. 8 is a decomposed perspective view illustrating the biosensor of FIG. 7.

FIG. 7 is a vertical sectional view illustrating a biosensor in another embodiment of the present invention. FIG. 8 is a decomposed perspective view illustrating the biosensor of FIG. 7 without a reaction reagent layer. This sensor is practically similar to the sensor shown in FIGS. 5 and 6, except that the spacer 43 is replaced by a sample solution induction layer 57 mainly composed of non-woven fabric. In the biosensor of this embodiment, a CMC layer 61 and a layer 64 including enzymes, a surface active agent, and an electron mediator are provided on the electrode system.

The following describes examples of the present invention.

EXAMPLE 1

A cholesterol sensor was produced as an example of the biosensors. The process first added a 0.5% by weight of aqueous solution of sodium carboxymethyl cellulose (hereinafter referred to as CMC) as the hydrophilic polymer dropwise onto the electrode system on the insulating base plate 1 shown in FIG. 1 and dried the solution in a hot blast drier at 50° C. for 10 minutes, so as to form a CMC layer 21. The process subsequently added 4 μl of an aqueous solution of potassium ferricyanide (corresponding to 70 mM potassium ferricyanide) as the electron mediator dropwise on to the CMC layer and dried the solution in the hot blast drier at 50° C. for 10 minutes, so as to form a potassium ferrocyanide layer 22.

The process then added 2 μl of a 2% by weight of ethanol solution of Triton X-100 as the surface active agent dropwise into a recess defined by the cover 8 and the slit 10 of the spacer 7, and dried the solution at room temperature for 3 minutes, so as to form a layer of the surface active agent. Triton X-100 was added to an aqueous solution in which cholesterol oxidase originating from Nocardia (EC1.1.3.6, hereinafter referred to as ChOD) and cholesterol esterase originating from Pseudomonas (EC. 3.1.1.13, hereinafter referred to as ChE) were dissolved. The process added 1.5 μl of the solution mixture onto the surface active agent layer, froze the layer with liquid nitrogen, and dried it in a Kjeldahl flask overnight in a freeze drier to give an enzyme/surface active agent layer 23 including 1 unit (U)/sensor cholesterol oxidase, 2.5 U/sensor cholesterol esterase, and 2% by weight of the surface active agent. The process then arranged a 2 mm×8 mm rectangular glass filter (GC50 manufactured by ADVANTEC LTD., thickness: 0.19 mm) at the position shown in FIG. 1 not to be in contact with the working electrode.

The through holes 14 and 15 and the notches 16, 16 were formed at the specific position with the filter of the sample solution supply pathway as shown in FIG. 1. This defined the area in which the surface of the filter was not in contact with any of the insulating base plate, the spacer, and the cover defining the sample solution supply pathway. The dimensions of these elements are specified previously with reference to FIG. 1.

As the sample solution, 20 μl of a whole blood sample was added dropwise onto the sample supply unit 12 of the base plate 1. Visual observations were made through the cover 8 composed of a transparent material to confirm that the liquid passing through the filter reached the outer circumferential part of the air vent 9 in the sample solution supply pathway. At 3 minutes after the confirmation, a pulse voltage of +0.5 V was applied to the working electrode in the direction of the anode with the counter electrode as the reference. The value of electric current was measured after 5 seconds. The result gave a response depending upon the concentration of cholesterol in serum.

The enzyme/surface active agent layer 23 was formed by the freeze drying method in this example, although it may be formed by the air drying method. In the latter case, however, the solubility of the reaction reagent layer is significantly worsened. It accordingly takes a long time until the reaction is completed after the filtered liquid reaches the outer circumference of the air vent 9 in the sample solution supply pathway.

EXAMPLE 2

In Example 1, the reaction reagent system was composed of the enzyme/surface active agent layer 23 formed by the freeze drying method on the rear face of the cover in the sample solution supply pathway and the CMC layer 21 and the potassium ferricyanide layer 22 formed by the air drying method at the specified position covering over the electrode system on the base plate. In this example, as shown in FIG. 4, the reaction reagent system was composed of a porous carrier 24, which was in contact with an end of the filter 11 and had enzymes, a surface active agent, and an electron mediator soaked therein and carried thereon, and the CMC layer 21 formed by the air drying method at the specified position covering over the electrode system on the base plate.

The arrangement of making part of the reagents included in the reaction reagent system carried on the porous carrier enhances the solubility of the reaction reagents into the sample solution, as in the case of the freeze drying method.

Like Example 1, the process first added a 0.5% by weight of aqueous solution of CMC as the hydrophilic polymer dropwise onto the electrode system and dried the solution in a hot blast drier at 50° C. for 10 minutes, so as to form the CMC layer 21.

The process bonded and fixed the porous carrier 24 made of felt which was cut into the size of 2×4.5 mm and mainly composed of glass filters at a specified position shown in FIG. 4 on the cover in the sample solution supply pathway with a cellulose-based adhesive (Cemedine C manufactured by Cemedine Co., Ltd), so as to be in contact with an end of the filter 11.

The process added 5 μl of the aqueous solution, in which cholesterol oxidase, cholesterol esterase, potassium ferricyanide, and Triton X-100 were dissolved as in the case of Example 1, dropwise onto the porous carrier 24, made the solution homogeneously soak into the porous carrier 24, and dried the solution in a hot blast drier at 50° C. for 15 minutes.

Like Example 1, the process located the filter and joined the cover member with the base plate 1 to complete a biosensor. The porous carrier 24 had the thickness of approximately 0.1 to 0.2 mm. The distance between the base plate 1 and the cover 8 in the part of the sample solution supply pathway closer to the electrode system was accordingly set equal to 0.3 mm, which was significantly greater than 0.1 mm in the structure of Example 1. In Example 2, GB100R was applied for the filter 11.

This biosensor showed a response corresponding to the concentration of cholesterol at three minutes after the dropwise addition of the whole blood sample to the sample supply unit.

In the above examples, the base plate 1 and the cover 8 were made of a transparent material, so that the flow-in state of the sample was observable with naked eyes.

In the above examples, the specific part of the slit 10 for forming the sample solution supply pathway with the filter fitted therein has a width equal to the width of the part that has the electrode system and receives a flow of the sample passing through the filter. One of these parts may be narrower than the other. FIG. 5 shows the positional relationship between the spacer and the filter and their shapes in such an example.

The arrangement of the reagents constituting the reaction reagent layer and their carrying method are not restricted to the specifications of the above examples, as long as the reagents in the reaction reagent system are quickly dissolved in the sample solution to ensure smooth progress of the enzyme reaction.

INDUSTRIAL APPLICABILITY

As described above, the present invention effectively prevents a solid component like hemocytes included in a sample solution from coming into contact with the electrode system and the reaction reagent system and thereby provide a biosensor that ensures highly accurate measurement and has a little variation in response.

What is claimed is:

1. A biosensor comprising:
   an insulating base plate,
   an electrode system that is provided on the base plate and has at least a working electrode and a counter electrode,
   a cover member that is combined with the base plate to define a sample solution supply pathway for leading a sample solution from a sample supply unit to the electrode system, wherein the sample supply unit is located on a side of the electrode system,
   a reaction reagent system including at least an oxidation-reduction enzyme and an electron mediator, and
   a filter in the sample solution supply pathway, the filter disposed between the electrode system and the sample supply unit,
   the biosensor having a space that encircles the surface of the filter in an area located between a first end of the filter close to the sample supply unit and a second end of the filter close to the electrode system, wherein said space has a width of 0.5 mm to 5.0 mm.

2. The biosensor of claim 1, wherein the cover member is disposed above the base plate, and the sample solution supply pathway starts from the sample supply unit provided on the base plate and is formed along the cover member and the base plate.

3. The biosensor of claim 1, wherein the space has a width of 1.0 mm to 3.0 mm.

4. The biosensor of claim 1, wherein the filter is a porous body having spaces connecting with one another in a three-dimensional manner, and the porous body moves blood from the sample supply unit toward the sample solution supply pathway by capillarity and functions to filter hemocytes based on a difference between the flow resistance of plasma and the flow resistance of hemocytes.

5. The bio sensor of claim 1, wherein the oxidation-reduction enzyme is cholesterol oxidase.

6. The biosensor of claim 1, wherein the reaction reagent system includes an enzyme having an ability of hydrolyzing cholesterol ester.

7. The biosensor of claim 6, wherein the enzyme having the ability of hydrolyzing cholesterol ester is cholesterol esterase.

8. The biosensor of claim 1, wherein the reaction reagent system includes a surface active agent.

9. The biosensor of claim 1, wherein part or all of the cover member and of the insulating base plate are transparent.

10. A biosensor comprising:
    an insulating base plate,
    an electrode system that is provided on the base plate and has at least a working electrode and a counter electrode,
    a cover member that is combined with the base plate to define a sample solution supply pathway for leading a sample solution from a sample supply unit to the electrode system, wherein the sample solution supply pathway is disposed in a direction of gravity from the sample supply unit provided on the cover member,
    a reaction reagent system including at least an oxidation-reduction enzyme and an electron mediator, and
    a filter in the sample solution supply pathway, the filter disposed between the electrode system and the sample supply unit, the biosensor having a space that encircles the surface of the filter in an area located between a first end of the filter close to the sample supply unit and a second end of the filter close to the electrode system, wherein the width of the space is not less that 100 $\mu$m and is smaller than the thickness of the filter.

11. The biosensor of claim 10, wherein the sample supply unit is located above the electrode system.

12. The biosensor of claim 10, wherein the filter is a porous body having spaces connecting with one another in a three-dimensional manner, and the porous body moves blood from the sample supply unit toward the sample solution supply pathway by capillarity and functions to filter hemocytes based on a difference between the flow resistance of plasma and the flow resistance of hemocytes.

13. The biosensor of claim 10, wherein the oxidation-reduction enzyme is cholesterol oxidase.

14. The biosensor of claim 10, wherein the reaction reagent system includes an enzyme having an ability of hydrolyzing cholesterol ester.

15. The biosensor of claim 14, wherein the enzyme having the ability of hydrolyzing cholesterol ester is cholesterol esterase.

16. The biosensor of claim 10, wherein the reaction reagent system includes a surface active agent.

17. The biosensor of claim 10, wherein part or all of the cover member and of the insulating base plate are transparent.

* * * * *

UNITED STATES PATENT AND TRADEMARK OFFICE
CERTIFICATE OF CORRECTION

PATENT NO. : 6,776,888 B2
DATED : August 17, 2004
INVENTOR(S) : Tomohiro Yamamoto et al.

It is certified that error appears in the above-identified patent and that said Letters Patent is hereby corrected as shown below:

Title page,
Item [87], PCT Pub. Date, should read as follows:
-- PCT Pub. Date: Feb. 7, 2002 --.

Column 12,
Line 39, "bio sensor" should read -- biosensor --

Signed and Sealed this

Nineteenth Day of April, 2005

JON W. DUDAS
*Director of the United States Patent and Trademark Office*